(12) United States Patent
Lyga et al.

(10) Patent No.: US 8,329,149 B2
(45) Date of Patent: Dec. 11, 2012

(54) TOPICAL LIGHTENING COMPOSITION AND USES THEREOF

(75) Inventors: John W. Lyga, Basking Ridge, NJ (US); Uma Santhanam, Tenafly, NJ (US); William J. Welsh, Princeton, NJ (US)

(73) Assignee: Avon Products, Inc., New York, NY (US)

( * ) Notice: Subject to any disclaimer, the term of this patent is extended or adjusted under 35 U.S.C. 154(b) by 11 days.

(21) Appl. No.: 12/975,415

(22) Filed: Dec. 22, 2010

(65) Prior Publication Data

US 2012/0003168 A1    Jan. 5, 2012

Related U.S. Application Data

(60) Provisional application No. 61/290,920, filed on Dec. 30, 2009.

(51) Int. Cl.
*A61K 31/74* (2006.01)
*A61K 8/46* (2006.01)

(52) U.S. Cl. ...................................................... 424/62

(58) Field of Classification Search .................. None
See application file for complete search history.

(56) References Cited

U.S. PATENT DOCUMENTS

| | | | |
|---|---|---|---|
| 5,932,229 | A | 8/1999 | Ptchelintsev et al. |
| 6,333,356 | B1 | 12/2001 | Ptchelintsev et al. |
| 2002/0141953 | A1 | 10/2002 | Ptchelintsev et al. |
| 2003/0069231 | A1 | 4/2003 | Rudolf et al. |
| 2006/0142358 | A1 | 6/2006 | Autier et al. |

OTHER PUBLICATIONS

Kubo, I et al.; Tyrosinase Inhibitors From Anacardium Occidentale Fruits; Journal of Natural Ptadvcts, Val. 57, No. 4,pp. 545-551, Apr. 1994.

Sakuma, K. et al.; Relationship Between Tyrosinase Inhibitory Action and Oxidation-Reduction Potential of Cosmetic Whitening Ingredients and Phenol Derivatives; Arch Pharm Res vol. 22, No. 4, 335-339, 1999.

Yang, F. and Boissy, Effects of 4-Tertiary Butylphenol on the Tyrosinase Activity in Human Melanocytes; Pigment Cell Res 1999; 12237-245.

Hearing, V. J. and Jimenez; Analysis of Mammalian Pigmentation at the Molecular Level Pigment Cell Research 275-85 (1989).

Shimizu, K. et al.; Inhibition of Tyrosianase by Flavonoids, Stilbenes and Related 4-Substituted Resorcinols: Structure-Activity Investigations; Planta Medica 66 (2000) 11-15.

Kubo, I. et al.; Flavonols from Heterotheca inuloides: Tyrosinase Inhibitory Activity and Structural Criteria: Bioorganic & Medicinal Chemistry 8 (2000) 1749±1755.

Perez-Gilabert, M. and Garcia-Carmona; Dimethyl Sulfide, a Volatile Flavor Constituent. Is a Slow-Binding Inhibitor of Tyrosinase; Biochemical and Biophysical Research Communications 285, 257-261 (2001).

Masamoto, Y, et al.; Mushroom Tyrosinase Inhibitory Activity of Esculetin Isolated From Seeds of Euphorbia Lathyris L.: Biosci Biotechnol Biochem 2003: 67 (3), 631-4.

*Primary Examiner* — Robert A Wax
*Assistant Examiner* — Jeffrey T Palenik
(74) *Attorney, Agent, or Firm* — Charles J Zeller; Joan M. McGillycuddy; David M. Joyal

(57) ABSTRACT

The disclosure relates to novel topical lightening compositions a skin depigmenting agent and a vehicle. There is provided a topical lightening composition comprising a substituted-4-oxobutanoic acid, ester, or amide tyrosinase inhibitor, and a vehicle. The depigmenting agents of this disclosure can be used as such or as a pharmaceutically acceptable salt including conventional non-toxic salts which include a metal salt or an alkaline earth metal salt, an ammonium salt, or an organic base salt. The depigmenting agents of this disclosure can be incorporated into any cosmetically-, dermatologically-, or cosmeticatically-acceptable vehicle or carrier normally used for topical application. The compositions and methods of the disclosure are effective to lighten skin, hair, lips, and/or nails.

31 Claims, No Drawings

TOPICAL LIGHTENING COMPOSITION AND USES THEREOF

This application claims priority to U.S. Provisional Patent Application Ser. No. 61/290,920 filed on Dec. 30, 2009.

TECHNICAL FIELD

The present disclosure relates to compositions useful in the cosmetic and cosmeceutical fields. In particular, a novel topical skin lightening composition is disclosed having substituted-4-oxobutanoic acids, esters, or amides as the active ingredient.

BACKGROUND

Skin color is principally determined by the concentration of melanin produced by the melanocytes. Synthesis of melanin starts with the conversion of the amino acid-L-tyrosine to 3,4-dihydroxyphenolalanine (L-DOPA) which, in turn, is oxidized to yield dopaquinone by tyrosinase (Kubo, I. et al. *J Nat Prod* 1994, 57, 545-551; Sakuma, K. et al. *Arch Pharm Res* 1999, 22, 335-9; Yang, F. and Boissy, R. E. *Pigment Cell Res* 1999, 12, 237-45). The catalytic action of the enzyme tyrosinase constitutes the rate-limiting step for melanin biosynthesis (Hearing, V. J. and Jimenez, M. *Pigment Cell Res.* 1989, 2, 75-85). Widely distributed in the plant and animal kingdom, tyrosinase is a multifunctional copper-containing enzyme (Shimizu, K. et al. *Planta Med* 2000, 66, 11-5) that mediates the coloring of skin, hair and eyes in animals as well as the familiar browning of fruits and vegetables (Kubo, I. et al. *Bioorg Med Chem* 2000, 8, 1749-55; Perez-Gilabert, M. and Garcia-Carmona, F. *Biochem Biophys Res Commun* 2001, 285, 257-61). Tyrosinase is also involved in the abnormal accumulation of melanin pigments (hyperpigmentation) on the skin or nails of people (Hearing, V. J. and Jimenez, M. *Pigment Cell Res.* 1989, 2, 75-85). Consequently, tyrosinase inhibitors such as kojic acid and albutin have been employed as important constituents of cosmetic products for skin lightening, skin whitening, and depigmenting hyperpigmentation and related conditions (Masamoto, Y. et al. *Biosci Biotechnol Biochem* 2003, 67, 631-4). More broadly, the utility of tyrosinase inhibitors has expanded in recent years to the food industry as well as medical products.

SUMMARY

Compositions and methods for lightening of the skin, particularly where the skin has hyperpigmentation or accumulated melanin pigments, are provided. The compositions comprise a substituted-4-oxobutanoic acid, ester, or amide skin depigmenting agent of Formula I:

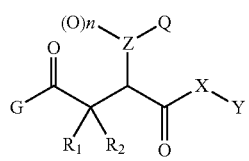

(I)

wherein, where Z is a sulfur atom or a group $NR^N$, wherein $R^N$ is selected from H, alkyl of 1 to 6 carbons, or cycloalkyl of 3 to 6 carbons, G is an aryl of 6 to 10 carbons optionally substituted with $R_3$-$R_4$;

$R_3$ represents, independently at each occurrence, a bond without $R_3$ or one of the following: (i) an aliphatic $C_1$-$C_{20}$ hydrocarbon radical; (ii) a $C_1$-$C_{20}$ aromatic hydrocarbon radical; or (iii) a $C_1$-$C_{20}$ heteroaryl radical;

$R_4$ is selected independently at each occurrence from hydrogen; —F; —Cl; —Br; —I; —OH, —OR; —NH$_2$; —NHR; —N(R)$_2$; —N(R)$_3^+$; —N(R)—OH; —N(O)(R)$_2$; —O—N(R)$_2$; —N(R)—O—R; —N(R)—N(R)$_2$; —C=N—R; —N=C(R)$_2$; —C=N—N(R)$_2$; —C(=NR)—N(R)$_2$; —SH; —SR; —CN; —NC; —CHO; —CO$_2$H; —CO$_2^-$; —CO$_2$R; —(C=O)—S—R; —O—(C=O)—H; —O—(C=O)—R; —S—(C=O)—R; —(C=O)—NH$_2$; —(C=O)—N(R)$_2$; —(C=O)—NHNH$_2$; —O—(C=O)—NHNH$_2$; —(C=S)—NH$_2$; —(C=S)—N(R)$_2$; —N(R)—CHO; —N(R)—(C=O)—R; —(C=NR)—O—R; —O—(C=NR)—R, —SCN; —NCS; —NSO; —SSR; —N(R)—C(=O)—N(R)$_2$; —N(R)—C(=S)—N(R)$_2$; —SO$_2$—R; —O—S(=O)$_2$—R; —S(=O)$_2$—OR; —N(R)—SO$_2$—R; —SO$_2$—N(R)$_2$; —O—SO$_3^-$; —O—S(=O)$_2$—OR; —O—S(=O)—OR; —O—S(=O)—R; —S(=O)—OR; —S(=O)—R; —NO; —NO$_2$; —NO$_3$; —O—NO; —O—NO$_2$; —N$_3$; —N$_2$R; —N(C$_2$H$_4$); —Si(—R)$_3$; —CF$_3$; —O—CF$_3$; —(C=O)—R; —PR$_2$; —O—P(=O)(OR)$_2$; —P(=O)(OR)$_2$; =O; =S; =NR; an aliphatic $C_1$-$C_{20}$ hydrocarbon radical; a $C_1$-$C_{20}$ aromatic hydrocarbon radical; or a $C_1$-$C_{20}$ heteroaryl radical;

$R_1$ and $R_2$ are each selected from: H, alkyl of 1 to 6 carbons, or cycloalkyl of 3 to 6 carbons;

X is oxygen or nitrogen;

Y is H, alkyl of 1 to 6 carbons; alkoxyalkyl of 2 to 12 carbons; or G substituted with $R_3$-$R_4$;

Q is alkyl of 1 to 10 carbons, cycloalkyl of 3 to 6 carbons, alkylaryl the alkyl of which has 1 to 6 carbons and said aryl has 6 to 10 carbons, or optionally substituted with $R_3$-$R_4$;

n is 0, 1, or 2, with the proviso that when Z is $NR^N$, n will be zero; and a cosmetically, dermatologically or pharmaceutically acceptable vehicle, whereby the amount of melanin in the skin is depleted over time.

The methods for effecting the lightening the skin, hair, lips, and/or nails comprise topically applying the foregoing compositions to the skin, hair, lips, and/or nails in an amount, and for a time sufficient to lighten the skin.

These and other objects and advantages of the present disclosure are provided by a topical lightening composition comprising an active ingredient that is a substituted-4-oxobutanoic acid, ester, or amide depigmenting agent, and a cosmetically-, dermatologically-, physiologically-, or cosmeceutically-acceptable vehicle.

Aspects of the present disclosure will become apparent to those skilled in the art after a reading of the following detailed description, including the illustrative embodiments and examples.

DETAILED DESCRIPTION

The instant disclosure provides novel topical lightening compositions with an active ingredient that is a substituted-4-oxobutanoic acid, ester, or amide skin depigmenting agent and uses thereof. One embodiment of the disclosure relates to lightening compositions comprising a skin depigmenting agent having the structure of Formula I:

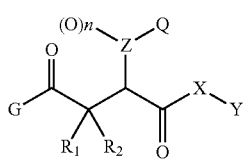

(I)

where Z is a sulfur atom or a group $NR^N$, wherein $R^N$ is selected from H, alkyl of 1 to 6 carbons, or cycloalkyl of 3 to 6 carbons, including without limitation, methyl, ethyl, n-propyl, isopropyl, n-butyl, iso-butyl, tert-butyl, pentyl, hexyl, cyclopropyl, cyclobutyl, cyclopentyl, and cyclohexyl;

where G is an aryl of 6 to 10 carbons optionally substituted with $R_3$-$R_4$;

where $R_3$ represents, independently at each occurrence, a bond (i.e., $R_3$ is absent) or one of the following: (i) an aliphatic $C_1$-$C_{20}$ hydrocarbon radical; (ii) a $C_1$-$C_{20}$ aromatic hydrocarbon radical; or (iii) a $C_1$-$C_{20}$ heteroaryl radical;

$R_4$ is selected independently at each occurrence from hydrogen; —F; —Cl; —Br; —I; —OH; —OR; —$NH_2$; —NHR; —$N(R)_2$; —$N(R)_3^+$; —N(R)—OH; —N(O)(R)$_2$; —O—N(R)$_2$; —N(R)—O—R; —N(R)—N(R)$_2$; —C=N—R; —N=C(R)$_2$; —C=N—N(R)$_2$; —C(=NR)—N(R)$_2$; —SH; —SR; —CN; —NC; —CHO; —CO$_2$H; —CO$_2^-$; —CO$_2$R; —(C=O)—S—R; —O—(C=O)—H; —O—(C=O)—R; —S—(C=O)—R; —(C=O)—NH$_2$; —(C=O)—N(R)$_2$; —(C=O)—NHNH$_2$; —O—(C=O)—NHNH$_2$; —(C=S)—NH$_2$; —(C=S)—N(R)$_2$; —N(R)—CHO; —N(R)—(C=O)—R; —(C=NR)—O—R; —O—(C=NR)—R, —SCN; —NCS; —NSO; —SSR; —N(R)—C(=O)—N(R)$_2$; —N(R)—C(=S)—N(R)$_2$; —SO$_2$—R; —O—S(=O)$_2$—R; —S(=O)$_2$—OR; —N(R)—SO$_2$—R; —SO$_2$—N(R)$_2$; —O—SO$_3^-$; —O—S(=O)$_2$—OR; —O—S(=O)—OR; —O—S(=O)—R; —S(=O)—OR; —S(=O)—R; —NO; —NO$_2$; —NO$_3$; —O—NO; —O—NO$_2$; —N$_3$; —N$_2$R; —N(C$_2$H$_4$); —Si(—R)$_3$; —CF$_3$; —O—CF$_3$; —(C=O)—R; —PR$_2$; —O—P(=O)(OR)$_2$; —P(=O)(OR)$_2$; =O; =S; =NR; an aliphatic $C_1$-$C_{20}$ hydrocarbon radical; a $C_1$-$C_{20}$ aromatic hydrocarbon radical; or a $C_1$-$C_{20}$ heteroaryl radical;

$R_1$ and $R_2$ are each selected from: H, alkyl of 1 to 6 carbons, or cycloalkyl of 3 to 6 carbons;

X is oxygen or nitrogen;

Y is H, alkyl of 1 to 6 carbons; alkoxyalkyl of 2 to 12 carbons; or G as defined above substituted with $R_3$-$R_4$;

Q is alkyl of 1 to 10 carbons, cycloalkyl of 3 to 6 carbons, alkylaryl the alkyl of which has 1 to 6 carbons and said the aryl of which has 6 to 10 carbons, or optionally substituted with $R_3$-$R_4$ as defined above; and n is 0, 1, or 2; with the proviso that when Z is $NR^N$, n will be zero.

Another embodiment is directed to lightening compositions comprising a 2-substituted thio-4-substituted-4-oxobutanoic acid, ester or amide skin depigmenting agent having the structure of Formula II:

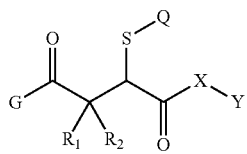

(II)

where G is an aryl of 6 carbons optionally substituted with alkyl of 1 to 4 carbons, a halogen, where the halogen is preferably chlorine, or an alkoxy of 2 to 4 carbons; Q is an aryl optionally substituted with halogen, where the halogen is preferably chlorine, an arylalkyl having an alkyl of 1 to 6 carbons and the aryl optionally substituted with a halogen or cycloalkyl having an alkyl of 3 to 6 carbons, X is oxygen or nitrogen; Y is H, alkyl of 1 to 6 carbons, or an alkoxyalkyl of 2 to 12 carbons, and $R_1$ and $R_2$ are each selected from H, alkyl of 1 to 6 carbons, or cycloalkyl of 3 to 6 carbons.

Another embodiment is directed to lightening compositions comprising a 2-substituted amino-4-substituted-4-oxobutanoic acid, ester or amide skin depigmenting agent having the structure of Formula III:

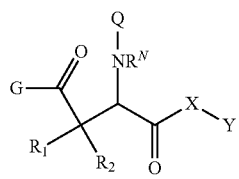

III where G is an aryl of 6 carbons optionally substituted with alkyl of 1 to 4 carbons, a halogen, where the halogen is preferably chlorine, or an alkoxy of 2 to 4 carbons; $R^N$ is selected from H, alkyl of 1 to 6 carbons, or cycloalkyl of 3 to 6 carbons; Q is an aryl optionally substituted with halogen, where the halogen is preferably chlorine; an arylalkyl having an alkyl of 1 to 6 carbons; arylheteroalkyl, and the aryl optionally substituted with a halogen or cycloalkyl having an alkyl of 3 to 6 carbons, X is oxygen or nitrogen; Y is H, alkyl of 1 to 6 carbons, or an alkoxyalkyl of 2 to 12 carbons, and $R_1$ and $R_2$ are each selected from H, alkyl of 1 to 6 carbons, or cycloalkyl of 3 to 6 carbons.

While not wishing to be bound, it is believed that the compounds of the skin depigmenting agents of the invention reduce the amount of melanin in skin through tyrosinase inhibition, although other mechanisms might be operative, alone or together with tyrosinase inhibition.

Enzymatic assays, such as but not limited to mushroom tyrosinase and B16 assays, measure tyrosinase inhibition, and are useful to identify skin depigmenting agents suitable in composition of the invention. Examples 1 and 2 describe more particulars of the methods. For example, the B16 assay use mice melanoma cells to measure tyrosinase inhibition. As the skilled artisan understands, other tyrosinase inhibitors useful in lightening compositions may be identified by these commonly used assays.

The compounds that are useful in the inventive lightening formulation inhibited melanin formation compared to control standards by a percent greater than about 20%, about 30%, about 40%, about 50%, about 70%, about 80%, about 85%, and about 90%. Preferred compounds inhibited melanin formulation by a percent greater than about 75%, about 80%, about 85%, about 87%, and about 90%.

Particular compounds found to be skin depigmenting agents useful in the disclosed lightening composition include, but are not limited to, those listed in Table 1:

TABLE 1

| | COMPOUND NAME |
|---|---|
| A | 2-(4'-chlorophenylthio)-4-(4'-t-butylphenyl)-4-oxobutanoic acid |
| B | 2-(4'-chlorophenylthio)-4-(4'-methylphenyl)-4-oxobutanoic acid |
| C | 2-(4'-chlorophenylthio)-4-(4'-ethoxyphenyl)-4-oxobutanoic acid |

TABLE 1-continued

| | COMPOUND NAME |
|---|---|
| D | 2-(4'-phenylthio)-4-(4' t-butylpheny)-4-oxobutanoic acid |
| E | 2-(4'-cyclohexylthio)-4-(4'-chlorophenyl)-4-oxobutanoic acid |
| F | 2-(4'-cyclohexylthio)-4-(4'-t-buytlpheny)-4-oxobutanoic acid |
| G | 2-(4'-chlorophenylmethylthio)-4-(4'-chlorophenyl)-4-oxobutanoic acid |
| H | 2-(4'-chlorophenylmethylthio)-4-(4'-ethoxyphenyl)-4-oxobutanoic acid |
| I | 2-(2-furanylmethylamino)-4-(4'-methylphenyl)-4-oxobutanoic acid |
| J | 2-(3-pyridylmethylamino)-4-(4'-methoxyphenyl)-4-oxobutanoic acid |
| K | 2-(benzylamino)-4-(4'-methylphenyl)-4-oxobutanoic acid | with compounds A-H being found to have high tyrosinase inhibition activity.

The topical compositions of the present disclosure, in particular, skin lightening compositions comprising the oxobutanoic acid compounds or salts thereof, are prepared by any customary methods known per se as described in WO 2004/060369 which is incorporated by reference herein.

Without being bound by theory, melanin synthesis is initially catalyzed by tyrosinase (i.e., tyrosine converted to L-3, 4-dihydroxyphenylalanine (DOPA), which is converted to DOPAquinone) and is then divided into eumelanogenesis or pheomelanogenesis. The compositions disclosed herein are believed to inhibit the enzyme tyrosinase from acting, thereby hindering melanin synthesis.

Another embodiment is directed to lightening compositions comprising pharmaceutically acceptable salts of the skin depigmenting agents exemplified in Formulas I and II, which are believed to inhibit tyrosinase activity. These salts are generally conventionally used non-toxic salts. Non-limiting examples of such salts include alkali metal salts or alkaline earth metal salts, ammonium salts, or organic base salts.

The topical composition disclosed herein may have an effective amount ranging from about 0.0001% to about 20% by weight of the oxobutanoic acid, ester or amide compound, about 0.001% to about 5%, about 0.01% to about 2.5% based on the total weight of the composition. The amount may be modified by the skilled practitioner depending on the specific application. However, in all of the compositions, an amount of the oxobutanoic acid, ester or amide skin depigmenting agent is present such that the resulting effect is a lightening of skin, hair or nails when applied to the surface in need of lightening. One embodiment is directed to a skin lightening composition which when applied to hyperpigmented skin results in a lightened color. In various embodiments the topical compositions contain about 0.05%, or about 0.1%, or about 0.5%, or about 1% by weight of the oxobutanoic acid based on the total weight of the composition.

Another embodiment relating to water based compositions, the oxobutanoic acid, ester or amide compound can be formulated in cosmetically-, dermatologically-, physiologically-, or cosmeceutically-acceptable pH range. For example, the pH of the lightening composition disclosed herein ranges from a pH of about 1 to about 8, a pH of about 2 to about 7, or a pH of about 3.5 to about 5.5. In various embodiments the pH of the composition is about 3, or about 3.5, or about 3.7, or about 4, or about 4.5, or about 5.

The compositions of the disclosure are suitable for topical use and therefore have a cosmetically-, dermatologically-, physiologically-, or cosmeceutically-acceptable carrier, vehicle or medium, i.e., one that is compatible with the topical surface, for example, skin, and allows for the absorption of the active component without causing irritation.

Another embodiment is directed to the methods of using the lightening compositions described herein. In particular, the methods are directed to the topical application of the lightening composition to keratinous surfaces, such as but not limited to the skin, hair, lips, and nails. The compositions of the present disclosure can be used to effectively lighten skin, hair, lips and nails by topically applying the composition having an effective amount of the topical lightening agent.

A further embodiment is directed to the topical lightening compositions of the present disclosure, and methods thereof, that treat a variety of skin conditions, including freckles, age spots, dark spots, hyperpigmentation, post-inflammatory hyperpigmentation, (e.g. post-acne hyperpigmentation), discoloration, melasma, yellowing, and dark circles under the eyes. Applying the lightening composition to skin in need thereof results in a uniformity or even skin tone, reduced size or intensity of distinct uniform areas of darker pigment, such as but not limited to, "age" spots, brown spots, and freckles, as well as the reduction, amelioration, or decreased intensity of mottled pigment or dark blotches, such as for example, sun spots. In one embodiment the composition is a face cream, and in an alternate embodiment the composition is a hand cream.

The topical lightening composition disclosed herein may be applied daily to see the most effect. In one embodiment, the lightening composition is applied one to two times a day, every day for at least one week, two weeks, three weeks, one month, six months or for years, to obtain and/or maintain the desired lightened effect. Another embodiment is directed to an application in the morning and another in the evening. The morning lightening formulation has, in addition to the disclosed tyrosinase inhibitor, UV blockers, antioxidents and other ingredients to counteract the harmful environmental stresses during daytime exposure. The nighttime application is useful since the skin repairs itself at night. The night-time formulation may contain additional moisturizers, and anti-aging ingredients to enhance skin repair. However, application requirements may be modified according to the desired result and timing for obtaining the desired result. The dosage and regimen will vary depending on the individual, severity of the condition to be alleviated. However, the practitioner would understand how to adjust and modify the dosage and time intervals.

One embodiment of the present disclosure relates to lightening compositions comprising skin depigment oxobutanoic acid, ester or amide compounds, or salts thereof, formulated into any form of a composition suitable for topical application including but not limited to creams, lotions, emulsions, gels, sprays, patches, masks, solids, liquid dispersions, foams, mousses, ointments, powders, pomades, towelettes, and the like.

In yet another embodiment, the oxobutanoic acid, ester or amide skin depigment agent and carrier of the composition are compatible with other ingredients that may be added for the various applications. The composition of the disclosure may also include any additive usually employed in the field envisaged for improving smoothness, spreadability, tack, fragrance, or other desirable cosmetic or cosmeceutical properties.

Another embodiment is directed to the present compositions which may include additional skin whitening agents known in the art. Non-limiting examples of useful agents include the following: hydroquinone, kojic acid, niacinamide, licorice and/or its derivatives, 1,3-thiodipropionic acid, oxa acid and oxa diacid, alpha and beta hydroxyl acids, ascorbic acid/ascorbic acid derivatives, arbutin, bearberry, *Glycyrrhiza glabra* and its derivatives, perilla leaf extract, and *Chlo-* rella vulgaris extract. Other useful whitening agents are disclosed in U.S. Pat. No. 5,980,904, which is incorporated herein by reference.

In addition, these compositions can be co-formulated with other cosmetic and dermatological additives and excipients familiar to those skilled in the art. For example, the disclosed lightening compositions may also include, but are not limited to, cosmetically or pharmaceutically active substances, moisturizers, UV protectants, antioxidants, anesthetics, anti-allergenics, antifungals, antimicrobials, anti-inflammatories, antiseptics, chelating agents, colorants, emollients, exfollients, film formers, fragrances, humectants, insect repellents, lubricants, moisturizers, pharmaceutical agents, preservatives, skin protectants, skin penetration enhancers, stabilizers, surfactants, thickening agents, skin modifiers, viscosity modifiers, vitamins, fragrances, oils, essential oils, essential fatty acids, liposoluble polymers, hydrocarbon polymers such as polyalkylenes and polyacrylates, and the like. Examples of such additives and excipients are set forth in the International Cosmetic Dictionary and Handbook, 11$^{th}$ Edition, Vol. 3, Section 3—Functions (Cosmetic, Toiletry, and Fragrance Association (CTFA), Washington D.C., 2006) ("INCI Handbook"), which is hereby incorporated by reference. (The CTFA is now known as the Personal Care Products Council.)

If the softness and elasticity of the composition are to be increased still further, it is also possible to add a plasticizer which is commonly added for cosmetic materials. Suitable materials may include both low-molecular weight and also high-molecular weight plasticizers which are optionally used, solubilized, or dissolved in a co-solvent.

Suspending and thickening agents typically include opacifying agents, cellulose derivatives, plasticizers, preservatives, solvents, surfactants; hectorites, waxes, gels, silica gels, gums and in particular xanthan gum, clays, organoclays, silica, fumed silica, fatty acid soaps, and various hydrocarbon gels, synthetic polymers such as an acrylic polymers or an associative polymer of the polyurethane type; and other ingredients incorporated into the disclosed composition as applied onto the surface of keratinous tissues.

Non-limiting examples of ingredients, such as emollients, that may preferably be used in the compositions of the disclosure include glycerine, propylene glycol, cyclomethicone, dimethicone, and emollients and other similar ingredients disclosed in the INCI Handbook.

Another embodiment is directed to the lightening composition of the disclosure comprising an amount of a pigment or colorant to hide the transition of skin color to a lighter shade. A pigment should be understood to mean inorganic or organic, white or colored particles. Coloring agents that may be used in the practice of the disclosure may include pigments, lakes, and dyes which are well known in the art and are disclosed in the INCI Handbook.

Compounds commonly used in the cosmetic arts for preventing or reducing fungal and/or microorganismal growth may also be added to the composition of the disclosure. By including these compounds, the shelf life of the composition is lengthened. These anti-fungal and anti-microorganisms include but are not limited to methyl paraben, butyl paraben, sodium dehydroacetate, and the like.

Although some of these materials may include an oily feeling and increased spreadability, as observed with some esters and organic sunscreens, the overall composition of the disclosure maintains its desired properties of transfer resistance, abrasion resistance, water and oil resistance, durability, flexibility, applicability, wearability, uniformity, sheen or gloss, drying time, adhesion, preferably in the absence of irritation.

The person skilled in the art will of course take care to choose the optional additional compounds and/or their quantities in such a way that the advantageous properties of the composition according to the disclosure are not, or are substantially not, impaired by the envisaged addition(s). In embodiments where these materials are added to the formulations of the disclosure to enhance the spreadability and the emollience of the product, however, it is preferred that the above materials be present in low enough concentrations for the formulation to retain its desired properties. These ingredients may be selected variously by the person skilled in the art in order to prepare a composition which has the desired properties, for example, consistency or texture. The choice of block copolymer film former, additional ingredients, and their concentrations may also be adjusted to vary the desired properties.

As used herein, "consisting essentially of" means that the composition or component may include additional ingredients, but only if the additional ingredients do not materially alter the basic and novel characteristics of the claimed compositions or methods. All percent are by weight of the total composition, unless otherwise indicated.

The contents of all patents, patent applications, published PCT applications and articles, books, references, reference manuals and abstracts cited herein are hereby incorporated by reference in their entirety to more fully describe the state of the art to which the disclosure pertains.

As various changes may be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings.

EXAMPLES

The following examples further describe and demonstrate embodiments within the scope of the present disclosure. The examples are given solely for the purpose of illustration and are not to be constructed as limitations of the present disclosure, as many variations thereof are possible without departing from the spirit and scope of the disclosure.

Example 1

Mushroom Tyrosinase Assay

Mushroom tyrosinase and L-Tyrosine were obtained from Sigma-Aldrich, Inc. (St. Louis, Mo.). The enzyme activity was measured in buffer containing 100 mM phosphate buffer pH 6.8, 5% absolute ethanol, 2 micrograms/milliliter mushroom tyrosinase, and 0.2 mg/ml L-Tyrosine. The reaction (conversion of L-Tyrosine to DOPAchrome) was conducted at 25° C. for 30 min, and absorbance was then measured at 500 nm. The inhibition assays were carried out in the presence of the test compound at 25 μM concentration for initial screening; those test compounds exhibiting inhibitory activity at this concentration were subjected to dose-response assays by varying the concentration (1-100 μM) for $IC_{50}$ determinations. Kojic Acid was used as a positive control inhibitor in these assays. The $IC_{50}$ values of the compounds, or the half maximal inhibitory concentration which is a measure of the effectiveness of a compound in inhibiting a biological or biochemical function, such as tyrosinase, that were tested ranged from about 6 to about 100 μM. The disclosed 2-substituted thio-4-substituted-4-oxobutanoic acid tyrosinase was selected for further testing.

Example 2

B16 Inhibition Assay

The B16 assay uses a cell line derived from mice with inhibition of tyrosinase as the end point. For the B16 assay, the active oxobutanoic acid tyrosinase inhibitors as disclosed herein in Table 1 were tested in a monolayer cell culture of B16 mouse melanoma cells. These cells are known to constitutively produce melanin and are a commonly utilized and accepted model system for monitoring the inhibition of melanin synthesis.

The B16 mouse melanoma cells were seeded (ATCC, cat. #: CRL-6475) into 96-well tissue culture-treated plates (BD Falcon) and treated with test actives diluted in DMEM without phenol red (Mediatech; cat. #: 17-205-CV) and examined for their ability to modulate pigment formation. Kojic acid was used as the positive control inhibitor. Cells were exposed to diluted test material or controls for 7 days. Following the treatment period, the level of pigment produced or melanin synthesized was quantified by reading the absorbance at 540 nm using a standard microplate reader (Tecan Group Ltd.).

After quantifying the amount of melanin, cell viability was determined using the MTT conversion method. The MTT conversion method measures the reduction of the MTT dye from a yellow colored, water-soluble, tetrazolium salt to a bluish-purple colored insoluble formazan precipitate by NAD(P)H-dependent microsomal dehydrogenase enzymes, which only function in viable cells. The intensity of the blue color is indicative of cell viability. After quantifying the amount of melanin pigment produced, the cells were exposed to MTT dye solution (1 mg/ml) for two to three hours. Formazan material was solubilized with reagent alcohol (95% ethanol: 5% isopropanol) and shaken on an orbital shaker for 15-30 minutes. MTT dye uptake and conversion by viable cells were determined by measuring the extracted formazan at 570 nm using a microplate reader. Total pigmentation was calculated, normalized to cell viability values and expressed as percent activity relative to control. The compounds A-H of Table 1 in a weight percent ranging from about 0.0002% to about 0.002% inhibited tyrosinase by a percent ranging from about 29% to about 87%. Each of the compounds A-H of Table 1 were found to be highly active in the B-16 assay. Data for compounds I-K is shown below in Table 2.

TABLE 2

| Compound | Concentration | B16 Results Percent inhibition of melanin |
|---|---|---|
| I | (0.001%) | −71% |
|   | (0.0001%) | −20% |
| J | (0.001%) | −53.63% |
|   | (0.0001%) | −27.84% |
| K | (0.001%) | −67% |
|   | (0.0001%) | −46% |

Example 3

Topical Lightening Compositions

TABLE 3

| | | Concentration (wt. %) | | | |
|---|---|---|---|---|---|
| Description | Purpose | Formula 1 | Formula 2 | Formula 3 | Formula 4 |
| Acrylates/C10-30 Alkyl Acrylate Crosspolymer | emulsifier | 1 | 1 | 1 | 1 |
| Cetyl Ethylhexanoate | emollient | 10 | 10 | 10 | 10 |
| C12-15 Alkyl Benzoate | emollient | 3.9 | 3.9 | 3.9 | 3.9 |
| Isopropyl Isostearate | emollient | 3 | 3 | 3 | 3 |
| Diisopropyl dimer dillinoleate | emollient | 0.1 | 0.1 | 0.1 | 0.1 |
| Tocopheryl acetate | antioxidant | 0.5 | 0.5 | 0.5 | 0.5 |
| Butylene glycol | humectant | 2 | 2 | 2 | 2 |
| Propylene glycol | humectant | 1 | 1 | 1 | 1 |
| Dimethicone PEG-7 isostearate | co-emulsifier | 0.5 | 0.5 | 0.5 | 0.5 |
| Methyl gluceth-20 | humectant | 0.5 | 0.5 | 0.5 | 0.5 |
| Triethanolamine | neutralizer | 1 | 1 | 1 | 1 |
| Acrylates/acrylamide copolymer/mineral oil | emulsifier | 1.5 | 1.5 | 1.5 | 1.5 |
| DMDM Hydantoin/Iodopropynyl butyl carbonate | preservative | 0.4 | 0.4 | 0.4 | 0.4 |
| Depigmenting agent selected from Table 1 | active | 0.3 | 0.03 | 0.01 | 0.005 |
| Deionized water | diluent | qs 100% | qs 100% | qs 100% | qs 100% |

What is claimed is:

1. A topical skin lightening composition, comprising a substituted-4-oxobutanoic acid, ester, or amide skin depigmenting agent of Formula I:

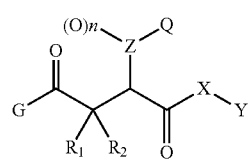

wherein, where Z is a sulfur atom or a group $NR^N$, wherein $R^N$ is selected from H, alkyl of 1 to 6 carbons, or cycloalkyl of 3 to 6 carbons, G is an aryl of 6 to 10 carbons optionally substituted with $R_3$-$R_4$;

$R_3$ represents, independently at each occurrence, a bond without $R_3$ or one of the following: (i) an aliphatic $C_1$-$C_{20}$ hydrocarbon radical; (ii) a $C_1$-$C_{20}$ aromatic hydrocarbon radical; or (iii) a $C_1$-$C_{20}$ heteroaryl radical;

$R_4$ is selected independently at each occurrence from hydrogen; —F; —Cl; —Br; —I; —OH, —OR; —NH$_2$; —NHR; —N(R)$_2$; —N(R)$_3^+$; —N(R)—OH; —N(O)(R)$_2$; —O—N(R)$_2$; —N(R)—O—R; —N(R)—N(R)$_2$; —C=N—R; —N=C(R)$_2$; —C=N—N(R)$_2$; —C(=NR)—N(R)$_2$; —SH; —SR; —CN; —NC; —CHO; —CO$_2$H; —CO$_2$; —CO$_2$R; —(C=O)—S—R; —O—(C=O)—H; —O—(C=O)—R; —S—(C=O)—R; —(C=O)—NH$_2$; —(C=O)—N(R)$_2$; —(C=O)—NHNH$_2$; —O—(C=O)—NHNH$_2$; —(C=S)—NH$_2$; —(C=S)—N(R)$_2$; —N(R)—CHO; —N(R)—(C=O)—R; —(C=NR)—O—R; —O—(C=NR)—R, —SCN; —NCS; —NSO; —SSR; —N(R)—C(=O)—N(R)$_2$; —N(R)—C(=S)—N(R)$_2$; —SO$_2$—R; —O—S(=O)$_2$—R; —S(=O)$_2$—OR; —N(R)—SO$_2$—R; —SO$_2$—N(R)$_2$; —O—SO$_3^-$; —O—S(=O)$_2$—OR; —O—S(=O)—OR; —O—S(=O)—R; —S(=O)—OR; —S(=O)—R; —NO; —NO$_2$; —NO$_3$; —O—NO; —O—NO$_2$; —N$_3$; —N$_2$R; —N(C$_2$H$_4$); —Si(—R)$_3$; —CF$_3$; —O—CF$_3$; —(C=O)—R; —PR$_2$; —O—P(=O)(OR)$_2$; —P(=O)(OR)$_2$; =O; =S; =NR; an aliphatic $C_1$-$C_{20}$ hydrocarbon radical; a $C_1$-$C_{20}$ aromatic hydrocarbon radical; or a $C_1$-$C_{20}$ heteroaryl radical;

$R_1$ and $R_2$ are each selected from: H, alkyl of 1 to 6 carbons, or cycloalkyl of 3 to 6 carbons;

X is oxygen or nitrogen;

Y is H, alkyl of 1 to 6 carbons; alkoxyalkyl of 2 to 12 carbons; or G substituted with $R_3$-$R_4$;

Q is alkyl of 1 to 10 carbons, cycloalkyl of 3 to 6 carbons, alkylaryl the alkyl of which has 1 to 6 carbons and said aryl has 6 to 10 carbons, or optionally substituted with $R_3$-$R_4$;

n is 0, 1, or 2, with the proviso that when Z is NR$^N$, n will be zero; and a cosmetically, dermatologically or pharmaceutically acceptable vehicle.

2. A topical skin lightening composition according to claim 1, wherein Z is NR$^N$.

3. A topical skin lightening composition according to claim 2, wherein R$^N$ is selected from the group consisting of methyl, ethyl, propyl, and butyl.

4. A topical skin lightening composition according to claim 2, wherein R$^N$ is methyl.

5. A topical skin lightening composition comprising a skin depigmenting agent of Formula II:

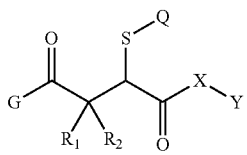

II wherein G is aryl of 6 carbons optionally substituted with alkyl of 1 to 4 carbons, halogen or alkoxy of 2 to 4 carbons; Q is aryl optionally substituted with halogen, arylalkyl said alkyl of 1 to 6 carbons and said aryl optionally substituted with halogen, or cycloalkyl said alkyl from 3 to 6 carbons; X is oxygen or nitrogen; Y is H, alkyl of 1 to 6 carbons, or an alkoxyalkyl of 2 to 12 carbons; and $R_1$ and $R_2$ are each selected from H, alkyl of 1 to 6 carbons, or cycloalkyl of 3 to 6 carbons; and a cosmetically, dermatologically or pharmaceutically acceptable vehicle.

6. A topical skin lightening composition comprising a skin depigmenting agent of Formula III:

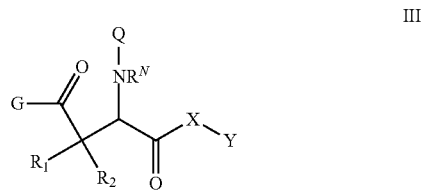

III wherein G is aryl of 6 carbons optionally substituted with alkyl of 1 to 4 carbons, halogen or alkoxy of 2 to 4 carbons; R$^N$ is selected from H, alkyl of 1 to 6 carbons, or cycloalkyl of 3 to 6 carbons, Q is aryl optionally substituted with halogen, arylalkyl said alkyl of 1 to 6 carbons and said aryl optionally substituted with halogen, arylheteroalkyl, or cycloalkyl said alkyl from 3 to 6 carbons; X is oxygen or nitrogen; Y is H, alkyl of 1 to 6 carbons, or an alkoxyalkyl of 2 to 12 carbons; and $R_1$ and $R_2$ are each selected from H, alkyl of 1 to 6 carbons, or cycloalkyl of 3 to 6 carbons; and a cosmetically, dermatologically or pharmaceutically acceptable vehicle.

7. The composition of claim 1, wherein said skin depigmenting agent is present in an amount of about 0.0001% to about 20% by weight.

8. The composition of claim 1, wherein said skin depigmenting agent is present in an amount of 0.001% to about 5% by weight.

9. The composition of claim 1, wherein said skin depigmenting agent is present in an amount of about 0.01% to about 2.5% by weight.

10. The composition of claim 1, wherein the skin depigmenting agent is present in an amount effective to lighten skin.

11. The composition of claim 1, wherein said composition has a pH ranging from about 1 to about 8.

12. The composition of claim 11, wherein said composition has a pH ranging from about 2 to about 7.

13. The composition of claim 11, wherein said composition has a pH ranging from about 3.5 to about 5.5.

14. The composition of claim 1, wherein said composition is in a product form of a cream, a lotion, an ointment, an emulsion, a gel, a foam, a mousse, a pomade, a solid, a powder, a spray, a liquid dispersion, a mask, a patch, or a towelette.

15. A topical skin lightening composition of claim 1, comprising a skin depigmenting agent selected from the group consisting of:

2-(4'-chlorophenylthio)-4-(4'-t-butylphenyl)-4-oxobutanoic acid;

2-(4'-chlorophenylthio)-4-(4'-methylphenyl)-4-oxobutanoic acid;

2-(4'-chlorophenylthio)-4-(4'-ethoxyphenyl)-4-oxobutanoic acid;

2-(4'-phenylthio)-4-(4'-t-butylphenyl)-4-oxobutanoic acid;

2-(4'-cyclohexylthio)-4-(4'-chlorophenyl)-4-oxobutanoic acid;

2-(4'-cyclohexylthio)-4-(4'-t-butylphenyl)-4-oxobutanoic acid;

2-(4'-chlorophenylmethylthio)-4-(4'-chlorophenyl)-4-oxobutanoic acid;

2-(4'-chlorophenylmethylthio)-4-(4'-ethoxyphenyl)-4-oxobutanoic acid;

2-(2-furanylmethylamino)-4-(4'-methylphenyl)-4-oxobutanoic acid;

2-(3-pyridylmethylamino)-4-(4'-methoxyphenyl)-4-oxobutanoic acid; and 2-(benzylamino)-4-(4'-methylphenyl)-4-oxobutanoic acid, and combinations thereof, and
a cosmetically, dermatologically or pharmaceutically acceptable vehicle.

16. The composition according to claim 15, wherein the skin depigmenting agent is 2-(4'-chlorophenylmethylthio)-4-(4'-chlorophenyl)-4-oxobutanoic acid.

17. The composition of claim 15, wherein said skin depigmenting agent is present in an amount of about 0.0001% to about 20% by weight.

18. The composition of claim 15, wherein the skin depigmenting agent is present in an amount effective to lighten skin.

19. The composition of claim 15, wherein said composition has a pH ranging from about 1 to about 8.

20. The composition of claim 15, wherein said composition is in a product form of a cream, a lotion, an ointment, an emulsion, a gel, a foam, a mousse, a pomade, a solid, a powder, a spray, a liquid dispersion, a mask, a patch, or a towelette.

21. A method comprising topically applying the composition of claim 1 to a keratinous surface in need of lightening.

22. A method according to claim 21, wherein said keratinous surface is skin, scalp, hair, or nails.

23. A method according to claim 21, wherein the composition is topically applied to treat a skin condition selected from the group consisting of freckles, age spots, dark spots, hyperpigmentation, post-inflammatory pigmentation, discoloration, yellowing, melasma, dark circles under the eyes, and any combinations thereof.

24. A method comprising topically applying the composition of claim 5 to a keratinous surface in need of lightening.

25. A method according to claim 23, wherein said keratinous surface is skin, scalp, hair, or nails.

26. A method according to claim 24, wherein the composition is topically applied to treat a skin condition selected from the group consisting of freckles, age spots, dark spots, hyperpigmentation, post-inflammatory pigmentation, discoloration, yellowing, melasma, dark circles under the eyes, and any combinations thereof.

27. A method comprising topically applying the composition of claim 15 to a keratinous surface in need of lightening.

28. A method according to claim 27, said keratinous surface is skin, scalp, hair, or nails.

29. A method according to claim 27, wherein the composition is topically applied to treat a skin condition selected from the group consisting of freckles, age spots, dark spots, hyperpigmentation, post-inflammatory pigmentation, discoloration, yellowing, melasma, dark circles under the eyes, and any combinations thereof.

30. A method of reducing pigmentation in a mammal, comprising administering to the mammal an effective amount of a compound as claimed in claim 1 or a pharmaceutically acceptable salt of ester thereof.

31. A method of inhibiting tyrosinase, comprising administering an effective amount of a compound as claimed in claim 1 or a pharmaceutically acceptable salt of ester thereof.

* * * * *